United States Patent [19]
Bradshaw et al.

[11] Patent Number: 5,882,291
[45] Date of Patent: Mar. 16, 1999

[54] DEVICE AND METHOD FOR CONTROLLING DOSE RATE DURING INTRAVASCULAR RADIOTHERAPY

[75] Inventors: Anthony J. Bradshaw, Missouri City; Richard V. Calfee, Houston, both of Tex.

[73] Assignee: Neocardia, LLC, Houston, Tex.

[21] Appl. No.: 762,740

[22] Filed: Dec. 10, 1996

[51] Int. Cl.$^6$ ........................................................ A61N 5/00
[52] U.S. Cl. ....................................................... 600/3
[58] Field of Search .............................................. 600/1–8

[56] References Cited

U.S. PATENT DOCUMENTS

| | | |
|---|---|---|
| 5,199,939 | 4/1993 | Dake et al. . |
| 5,498,227 | 3/1996 | Mawad ........................................ 600/3 |
| 5,540,659 | 7/1996 | Teirstein . |

FOREIGN PATENT DOCUMENTS 9102312.2  8/1992  Germany .

OTHER PUBLICATIONS

Discoveries in Radiation for Restenosis, course presented by The Andeas Gruentzig Cardiovascular Center et al, Emory University, (1996), Weinberger, M.D., Ph.D, Abstract 14, p. 39–41.

Discoveries in Radiation for Restenosis, course presented by The Andreas Gruentzig Cardiovascular Center et al, Emory University Schopohl, B. et al, (1996), Abstract 29, pp. 89–92.

Discoveries in Radiation for Restenosis, course presented by The Andreas Gruentzig Cardiovascular Center et al, Emory University (1996), Waksman, MD, Abstract 30, pp. 93–94.

Vascular Brachytherapy (1996) editor, Waksman et al, Chapter 29, pp. 273–278.

Int. J. Radiation Oncology Biol. Phys., vol. 29, No. 1, pp. 183–186, 1994.

*Primary Examiner*—John P. Lacyk
*Attorney, Agent, or Firm*—Blank Rome Comisky & McCauley LLP

[57] ABSTRACT

A method is disclosed for treating a blood vessel which has been subjected to interventional dilatation, to inhibit restenosis that would otherwise occur from cellular proliferation attributable to traumatic response at the site of the vessel interior wall where the dilatation was performed. The method includes introducing a radioactive source into the blood vessel so that the source is positioned adjacent to the site, and exposing targeted tissue of the vessel interior wall at the site to said radioactive source for a period of time sufficient to deliver a prescribed dose of radiation to the tissue. The rate at which the prescribed dose is delivered to the targeted tissue is adjusted to positively assure that the rate is held in a range with an upper limit of about 60 rads per second. Dose rate adjustment is controlled by selectively setting the distance between the source and the targeted tissue, or by appropriately selecting the length of the source according to the length of the site of targeted tissue along the vessel interior wall, and/or by appropriately attenuating the radiation emitted by the source to a desired reduced magnitude at the site of the targeted tissue, to positively assure that the dose rate delivered to the targeted tissue will not exceed 60 rads per second.

6 Claims, 1 Drawing Sheet

DEVICE AND METHOD FOR CONTROLLING DOSE RATE DURING INTRAVASCULAR RADIOTHERAPY

BACKGROUND OF THE INVENTION

The present invention relates generally to intravascular radiotherapy, and more particularly to improved devices and methods for delivering nuclear radiation therapy to avoid restenosis in blood vessels that have been subjected to an interventional dilatation procedure.

U.S. Pat. No. 5,199,939 to Dake et al. discloses a technique for inhibiting restenosis in a coronary artery following angioplasty by delivering nuclear radiation therapy to the artery wall at the time or immediately after the angioplasty procedure is performed.

In co-pending patent applications Ser. Nos. 08/057,322, 08/339,950 and 08/467,711 of A. J. Bradshaw et al., which are assigned to a common assignee, and incorporated herein by reference in their entirety, devices and techniques are disclosed for improved delivery of intravascular radiotherapy by substantially centering the radioactive source in the tortuous pathway of a coronary artery to provide a relatively uniform dose of radiation to preselected tissue of the arterial wall at the target site in a substantially circumferential band disposed a predetermined radial distance from the radioactive source. It is essential that a uniform dose of radiation be delivered to the preselected tissue in the designated circumferential band about the source, rather than a random or non-uniform dose. Otherwise, tissue segments at locations on the interior surface of the wall closer to and further from the source would be overdosed and underdosed, respectively. Overdosing is to be avoided because it causes excessive vessel hemorrhaging, excessive fibrous media thinning, and the possibility of aneurysm or other late radiation effects. J. Weinberger et al. of Columbia University have suggested in a published study that overdosing also may be slightly stimulative in some dose ranges. Underdosing should also be avoided because it does not inhibit the proliferative cellular growth which is a traumatic response to the initial interventional dilatation, and hence, does not substantially deter restenosis.

In a clinical setting, it is desirable to administer the intravascular radiotherapy in as short a time as is practicable, to avoid the blood flow reduction and other factors which can lead to adverse consequences from leaving the catheter and radioactive source (so-called source wire) in place in the coronary artery or other portion of the vasculature for too long a time. Treatment time may be shortened by increasing the activity level of the radioactive source.

Studies by the Frankfort Group and Emory University have indicated that very high activity radioactivity sources stepped through the target site with relatively short treatment times, i.e., where the source is of shorter length than the length of arterial wall which is to be treated and must therefore be incrementally advanced (or retracted)—or "stepped"—through the target site during treatment, have yielded mixed results. Neither of these cited studies used techniques to assure centering of the radioactive source, and each used a standard oncology catheter in delivery of the radiation. Research conducted by the applicants herein using a high activity stepping source without centering to treat coronary arteries in pigs yielded mixed results, with the relatively straight circumflex (CFX) and left anterior descending (LAD) arteries exhibiting a dose response with 1000 rads (r, or centiGray, cGy) which is similar to the control arteries. A better response was achieved with 1500 r, and even better with 2500 r. In that regard, the term "better" is used as reflecting improved results in percentage of area stenosis, in maximal intimal thickness, and in mean luminal area, compared to control. The right coronary artery (RCA) results showed no dose response and no improvement at any of the three doses, thought by the applicants to be attributable to lack of dose control in this severely curved artery because no centering mechanism was used to preclude random overdosing and underdosing.

Further testing and data analysis by the applicants has suggested another mechanism responsible for the poor RCA results and the mixed results encountered in other high activity studies. It is a primary objective of the present invention to provide improvements in the methods and apparatus for inhibiting restenosis in blood vessels subjected to angioplasty procedures.

SUMMARY OF THE INVENTION

The applicants herein have discovered that the dose rate, i.e., the rate at which the prescribed dose of radiation is delivered from the radioactive source to targeted tissue at the interior of the vessel wall, to be effective, should not exceed 60 rads per second. Radiation dosage exceeding this rate produces robust cellular proliferation, even in arteries which had not been previously subjected to dilatation and higher doses of radiation. This proliferative effect, which is highly undesirable, is clearly evident in previously dilatated pig arteries (e.g., balloon overstretch model), is dominant at doses which are effective at lower dose rates, and causes the vessel lumen to be restricted and even to close rather than to remain open as sought by the application of intravascular radiotherapy.

Accordingly, a method is provided for treating a blood vessel which has been subjected to interventional dilatation, to inhibit restenosis that would otherwise occur from cellular proliferation attributable to traumatic response at the site of the vessel interior wall where the dilatation was performed. The method includes treating the patient to irradiate targeted tissue along a length of the interior surface of the wall of a blood vessel subjected to an interventional dilatation procedure, including prescribing a dose of radiation to be delivered from a radioactive source to tissue along the length of interior surface to inhibit cellular proliferation thereat, selecting a radioactive source having an activity level sufficient to deliver the prescribed dose to the targeted tissue, placing the radioactive source within the vessel adjacent to targeted tissue for a time interval required to deliver the prescribed dose thereto, and maintaining certain predetermined characteristics of the source relative to the targeted tissue to assure that the prescribed dose is delivered to the targeted tissue at a rate which does not exceed a maximum value of approximately 60 rads per second at the prescribed treatment distance.

The maintaining of certain predetermined characteristics of the source relative to the targeted tissue includes selecting at least one of the configuration of the source, the position of the source in the vessel relative to targeted tissue, the distance between the source and targeted tissue adjacent thereto, and the attenuation of radioactivity emitted by the source at the adjacent targeted tissue, to limit the rate at which the prescribed dose is delivered to targeted tissue so as not to exceed the specified maximum value. Control of attenuation of radioactivity emitted by the source may be accomplished by interposing sufficient radiation-attenuating material between the source and the targeted tissue to limit the rate of delivery of the prescribed dose.

In a preferred method, the radioactive source is a beta emitter. Preferably also, the radioactive source is a solid material secured to a thin, elongate, flexible line to permit the source to be advanced into and retracted from the vessel from a control point outside the patient's body, generally be means of a conventional afterloader which can be operated from a remote location with respect to the patient being treated. Alternatively, the radioactive source may comprise pellets, powder, or liquid, or even gaseous material. Pellets, for example, may be introduced into a catheter under pressure from an external device to position them in a desired location for treating targeted tissue. In yet another form, the radioactive source may be implemented in the form of a stent which is implanted in a blood vessel at the target site.

BRIEF DESCRIPTION OF THE DRAWINGS

Although it is not necessary to present drawings to enable a full understanding of the present invention, the above and still further objects, features, aims, and advantages of the invention will become apparent from a consideration of the following detailed description of the invention, taken in conjunction with the accompanying drawings, in which.

DETAILED DESCRIPTION OF THE PREFERRED METHODS AND EMBODIMENTS

Figure 1:
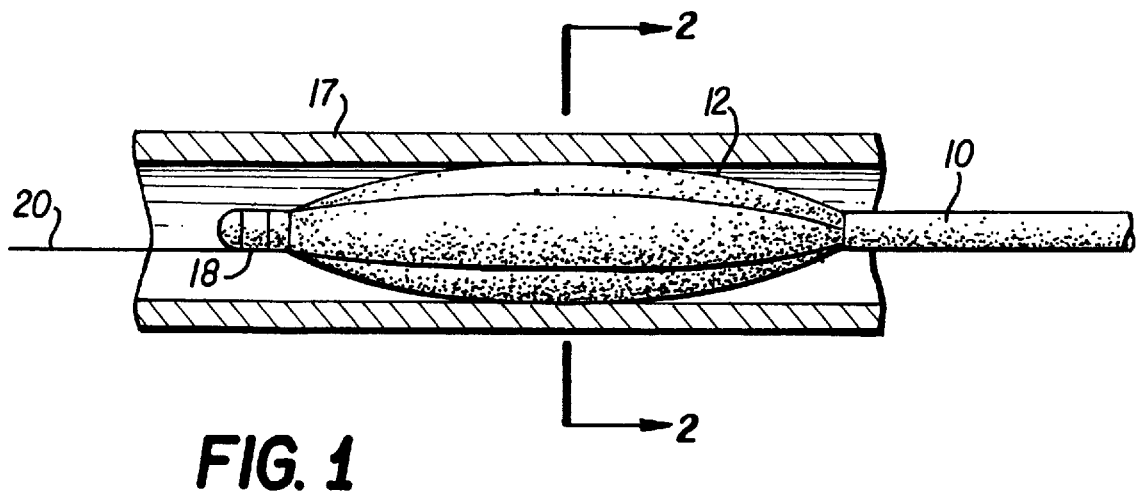
FIG. 1 is a side view, partly in section, of a radioactive source disposed in a catheter in a portion of a blood vessel targeted for delivery of a prescribed dose of radiation to tissue at the interior of the vessel wall, including means for centering the source in the lumen of the vessel to assure a delivery of uniform dose to tissue in a circumferential band of tissue of the interior wall about the radioactive source.

As noted above, the present invention provides for the delivery of a prescribed dose of nuclear radiation to targeted tissue at the interior surface of the blood vessel wall site which has been subjected to a procedure for opening the lumen of the vessel, as an interventional dilatation procedure, whether the opening is achieved by performing an angioplasty procedure (using a balloon, a laser, or a rotating ultra-sharp blade, for example), or by stenting, or by use of any other means. The targeted tissue preferably lies in a substantially circumferential band about the radioactive source used to deliver the radiation, the source being introduced into the patient's vascular system for positioning at the target site within the blood vessel. The essence of the invention is that the dose rate of the radiation to which the preselected tissue is subjected during delivery is pro-actively limited to a value not exceeding 60 rads per second.

It is important to understand clearly that limiting the dose rate is not the same as limiting the dose which is prescribed by the attending physician or physicist for a successful result of the procedure, as in inhibiting restenosis in the vessel in response to the trauma suffered during an angioplasty procedure. Thus, the significance of the invention lies in a recognition that although the dose absorbed by the preselected tissue may be appropriate and in the amount prescribed, the radiation procedure will be unsuccessful, and, indeed, may exacerbate the extent or onset (or both) of cellular proliferation sought to be avoided, if the rate at which that dose is delivered exceeds a particular value, and specifically, if the dose rate exceeds 60 rads per second.

Radiation dose is a function of the isotope (i.e., the energy spectrum and tissue absorption for that energy), the distance of the target tissue from the radioactive source, and the amount of time over which the target tissue is exposed to the radiation. The device characteristics and the methods employed for limiting and controlling the dose rate are described below.

One technique for setting the dose rate is to control the distance from the radioactive source to the targeted tissue. Suppose, for example, that the dose prescribed for absorption by the interior arterial wall tissue is 3000 rads, for a treatment length (of arterial wall at the target site) of 30 millimeters (mm), and that the activity of the source on the treatment day (i.e., source activity inevitably declines as a consequence of continuing decay, unless recharged or reactivated by subjection to additional nuclear irradiation which is not practical for a source to be available at a treatment center (hospital or otherwise) for use at any time during a predetermined period of suitable activity) is such that the prescribed dose will be delivered in two minutes to a 4 mm diameter artery. The dose rate is 1500 rads per minute (dose/time for delivery, or 3000/2), or 25 rads per second, provided that the source is centered in the artery. As observed earlier herein, if the source is not centered the tissue of the arterial wall will be subjected to overdosing at the side nearest the source, and to underdosing at the side furthest from the source. In the latter circumstances, the dose rate will vary accordingly, the rate being faster at the near side (higher dose delivered in the prescribed time interval) and slower at the far side (lower dose delivered in that same interval).

The dose is calculated, and the time interval over which the source is to be situated in the treatment volume is determined, based on a measure of diameter of the blood vessel obtained from fluoroscopy or from intravascular ultrasound. If the catheter is not restrained and the source is placed against the wall of the catheter in the vessel, the dose will approximately triple to 9000 rads, and so will the dose rate—to 75 r/sec. The segment of the vessel wall in contact with the catheter may suffer radiation damage, in addition to undergoing excessive cellular proliferation in less than 30 days, which may negate some or all of the gain in lumen area that had been achieved by virtue of the original angioplasty that had prompted the need for radiation treatment.

Figure 2:
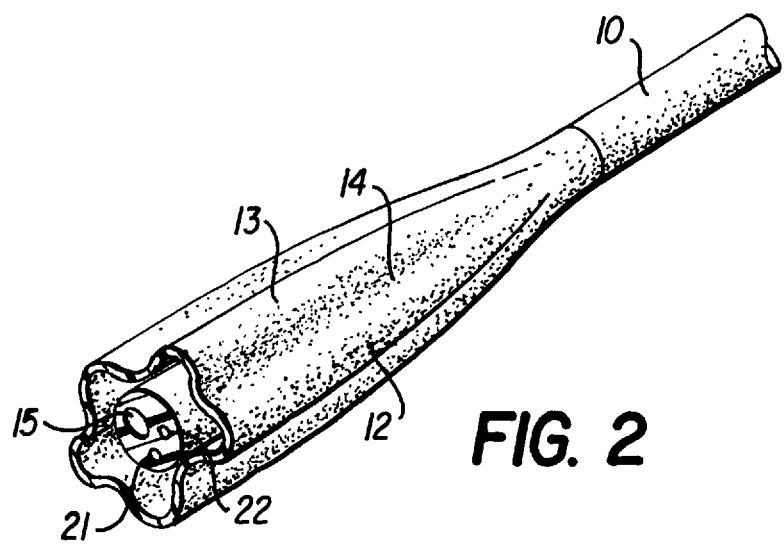
FIG. 2 is a perspective view, in section taken along the lines 2—2 of FIG. 1.

To overcome this problem, the source should be maintained at a known minimum distance from the targeted tissue, preferably centered radially in the dilatated targeted segment or portion of the length of the artery by use of a balloon catheter 10 with a corrugated balloon membrane 12 whose undulations (such as 13, 14) permit a flow-through of blood in the trough between each pair of crests to enable perfusion when in place and inflated in the blood vessel, as shown in FIGS. 1 and 2. Although not clearly shown in the Figure, each trough is fastened to the catheter 10 internally of the membrane 12 to maintain an open passage for blood flow externally of the membrane. A lumen 15 of the balloon catheter is substantially centered longitudinally in the blood vessel 17 so as to also center the radioactive source 18 of a source wire 19, which is to be advanced and retracted via balloon catheter 10 during use throughout the radiotherapy procedure. The source is centered in lumen 15 of the catheter, and since the lumen of the catheter is centered in the vessel (with appropriate biasing at 20 to compensate for the offset of lumen 15 from the longitudinal center of the balloon membrane), the source is also centered longitudinally in the vessel. The centering scheme tends to assure that targeted tissue at the site of the interventional dilatation of the blood vessel lumen will be uniformly irradiated in a circumferential band about the radioactive source, as disclosed in the aforementioned co-pending applications 08/057,322, 08/339,950 and 08/467,711. A pair of additional lumens 21 and 22 are used for a guidewire and for balloon inflation/deflation, respectively.

Another technique for setting the dose rate is to control or mandate the configuration of the radioactive source relative to configuration of the selected tissue. To that end, the source length is set according to the length of the artery wall segment to be treated. For example, assume that the source in the above illustration is centered at a known minimum distance from the target. If the source is 10 mm long, it must be stepped longitudinally so that the dose of 3000 rads may be delivered in two minutes to the 30 mm long segment of the 4 mm diameter artery. In particular, the source must be stepped through three sequential 10 mm positions along the 30 mm targeted segment of the artery wall, within a two minute period. In those circumstances, however, the dose rate to the target or preselected tissue along the length of the arterial wall segment being treated An would be 75 r/sec, since each one-third portion of that segment must receive a prescribed dose of 3000 rads during the short interval that the source is adjacent that portion (3000 rads/2 mins÷60 secs÷1/3=75 r/sec).

In this instance, the solution to maintaining the dose rate below the 60 r/sec limit is to increase the length of the radioactive source sufficiently to make it more nearly equal to the length of arterial wall segment to be treated. In particular, the source length should be increased (i.e., by selecting the length in advance according to the measured length of segment of the arterial wall to be treated) so that any segment of the smallest artery which is anticipated to be treated with radiotherapy will receive the prescribed dose of radiation at a dose rate which is less than 60 r/sec. The length of the source need not be the same as the length of the vascular wall segment or portion to be treated; only a length sufficient to assure that the dose rate is less than that maximum value.

Yet another technique for controlling the dose rate is to employ a suitable radiation attenuating material between the source and the tissue to be treated, such that the dose rate applied to the target tissue is appropriately limited to a value less than 60 r/sec. For illustration, assume that access is available to only a high activity oncology brachytherapy device to perform peripheral vascular procedures, or, alternatively, that an unusually small vessel is to be treated with the beta source coronary intravascular radiotherapy system of the previous example. In either case, the dose rate for tissue located at the target distance from the source is likely to exceed 60 r/sec. The solution to this problem is to employ radiation-attenuating material in the treatment catheter that will adequately reduce the rate at which the prescribed dose will be delivered to the targeted tissue, to a value below the specified upper limitation.

For example, the catheter material may be modified to contain a high Z filler (high density) such as barium for beta sources, or materials such as a wound coil layer of tungsten wire through the treatment length of the catheter to appropriately attenuate gamma radiation-emitting sources. Alternatively, or additionally, the balloon centering device could be filled with an appropriate attenuating liquid. In all such cases, the radiation-attenuation characteristics of the material must be known and taken into consideration for calculation of the dose rate that will then apply for the particular source which is used in the radiotherapy procedure. It is to important to note that different materials have drastically different attenuation properties relative to the entire family of radioactive isotopes. The idea is to utilize attenuating material in the treatment catheter or other convenient region between the source and the targeted tissue as necessary to reduce the dose rate to an acceptable level, without substantially impeding perfusion at the target site.

As has been noted above in the summary of the invention, the radioactive source need not be restricted to a source wire with a solid source fastened to a thin, elongate, flexible line, although that is the preferred configuration. Instead, the source may be implemented in alternative form, such as pellets which are injected by hydraulic means after the catheter is installed in the blood vessel, or any other known form described in the prior art, including powder, liquid, or gas. The source may be carried by a stent which is deployed to provide the interventional dilatation to hold open the venous lumen.

In the aforementioned Dake et al. '939 patent, an exemplary treatment is described in which the prescribed maximum dose is about 2500 rads, and the maximum dose rate is about 10,000 rads per hour (equivalent to about 2.78 rads per second) measured at 3 mm from the longitudinal central axis of the carrier. That maximum dose described in Dake et al. can be delivered in 15 minutes to tissue located at 3 mm from the central axis (and from the source, if the source is positioned at the central axis), i.e., 2500 rads÷2.78 rads per second=899 seconds (substantially equivalent to 15 minutes). For targeted tissue closer to the radioactive source than 3 mm, the dose rate presumably would increase. If a phosphorus isotope $P^{32}$) were used as the source, the dose rate at a point located 1 mm from the source would be approximately 31 r per sec, which is well within the maximum dose rate of 60 r/sec according to the present invention. However, the maximum dose of 2500 rads in Dake et al may be insufficient for beta emitting sources, depending on how the Dake et al. point of prescription for dose is interpreted.

Animal studies conducted by the applicants herein, using the beta emitter $P^{32}$ in pig coronary arteries, have shown that at least about 2000 rads are needed at the adventia to inhibit cellular proliferation and resultant lumen shrinkage. A dose of 2000 at the adventia requires a dose at the vessel surface of at least about 2750 rads. The Dake et al. disclosure does not indicate the precise point in the vessel wall for which such a dose would be prescribed, nor teach a maximum dose as great as 2750 rads. Indeed, other researchers have speculated that the effective dose is less than 2500 rads. Other beta emitters such as Yttrium 90 ($Y^{90}$) and Strontium 90 ($Sr^{90}$, which produces the daughter of $Y^{90}$) have slightly higher maximum energies and therefore exhibit slightly different dose rates at distance curves than $P^{32}$, but the same dose and dose rate requirements are present.

Good results have been produced by the applicants herein with 3000 rads to the adventia (even up to about 4800 rads) without significant radiation damage to the vessel in the treated area. The results were found to be good in both balloon injured arteries and in arteries where a stent had been placed prior to irradiation. The results were achieved using a centering balloon, and the effective doses for beta emitters were found to be much higher than had been speculated in the prior art.

Even though the required dose is higher than anticipated by Dake et al. and others, it remains highly desirable to hold the treatment time to less than 15 minutes, and preferably less than 10 minutes. A beta source may be chosen from the group comprising $P^{32}$, $Y^{90}$, and $Sr^{90}$, or the predominant beta emitter tungsten 188 ($W^{188}$) or daughter rhenium 188 ($Re^{188}$). The dose to be delivered should be in the range of at least about 2000 rads to as much as about 5000 rads to a point about 0.5 mm deep into the surface of the artery lumen along the entire length of a previously dilatated artery, at a dose rate not exceeding 60 r/sec, with a total treatment time of 15 mins (preferably 10 mins) to deliver the dose. A minimum dose rate may be calculated as nominally about 3.1 r/sec ((2750 rads/15 mins)÷60 secs), making a usable dose rate range according to the present invention of from about 3.0 to about 60 r/sec. A point located at 0.5 mm deep into the interior surface of the artery adjacent the lumen serves for present purposes to describe the adventia generically, but disregards the fact that in a previously dilatated artery the plaque makes the distance to the adventia vary relative to the center of the resultant lumen after angioplasty.

The effective dose of gamma emitting sources appears to be less than that of the beta emitting sources, which is probably attributable to the greater dose to the adventia relative to the surface dose, as the activity of gamma emitters does not drop off as rapidly as that of beta emitters. In any event, although it is not altogether clear that the maximum dose rate for gamma emitters is 60 r/sec, for purposes of the claims herein it is assumed that such threshold applies to the gamma sources as well as the beta sources.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. A method of treating targeted tissue of the body of a patient with ionizing radiation to inhibit proliferation of the targeted tissue and to avoid unintended exacerbated proliferation of the targeted tissue, including the steps of:

prescribing the radiation dosage to be delivered to the targeted tissue;

selecting a source of radiation from which said prescribed dosage is to be delivered and a set of physical parameters affecting the time rate at which radiation will be delivered from the selected source to the targeted tissue including the configuration of the source relative to the configuration of the targeted tissue, the distance between the selected radiation source and the targeted tissue during irradiation thereof, and the radiation attenuation characteristics of the medium residing between the radiation source and the targeted tissue, and canceling treatment of the targeted tissue with the selected radiation source before the prescribed radiation dosage has been delivered to the targeted tissue if the time rate of delivery of said dosage is determined to exceed approximately 60 rads per second.

2. The method of claim 1, wherein the method is treating targeted tissue at a predetermined site along the inner lining of a coronary artery which has undergone an angioplasty procedure, to inhibit restenosis thereof, and the steps of the method include determining the distance between the selected radiation source and the targeted tissue during irradiation, from the physical dimensions of the source when centered along the longitudinal axis of the lumen, and from the diameter of the lumen at the site of the targeted tissue.

3. The method of claim 2, including selecting a beta emitter as said radiation source.

4. The method of claim 2, including selecting a gamma emitter as said radiation source.

5. The method of claim 2, including securing the radiation source to an elongate, flexible line for advancement and retraction of the radiation source into and from the artery in the course of treatment.

6. The method of claim 1, including continuing treatment of the targeted tissue with the selected radiation source until the prescribed radiation dosage has been delivered to targeted tissue for so long as the time rate of delivery of the radiation is in a range from not less than about 3 rads per second to not more than about 60 rads per second.

* * * * *